United States Patent
Bourke

(10) Patent No.: US 8,454,568 B2
(45) Date of Patent: Jun. 4, 2013

(54) APPARATUS AND METHOD FOR THE REMOVAL AND CONTAINMENT OF HUMAN WASTE EXCRETION

(75) Inventor: Edward Bourke, Boynton Beach, FL (US)

(73) Assignee: Osto Innovations, LLC, Lantana, FL (US)

( * ) Notice: Subject to any disclaimer, the term of this patent is extended or adjusted under 35 U.S.C. 154(b) by 384 days.

(21) Appl. No.: 12/789,220

(22) Filed: May 27, 2010

(65) Prior Publication Data

US 2011/0022011 A1    Jan. 27, 2011

Related U.S. Application Data

(60) Provisional application No. 61/181,590, filed on May 27, 2009.

(51) Int. Cl.
*A61M 1/00* (2006.01)
(52) U.S. Cl.
USPC ............................................ 604/327; 4/144.3

(58) Field of Classification Search
USPC ................. 604/319, 327, 329, 331, 346, 349, 604/351; 4/144.1–144.4
See application file for complete search history.

(56) References Cited

U.S. PATENT DOCUMENTS

| 5,334,174 | A |   | 8/1994  | Street            |
|-----------|---|---|---------|-------------------|
| 5,681,297 | A |   | 10/1997 | Hashimoto         |
| 2003/0093856 | A1 |   | 5/2003  | Tanaka        |
| 2005/0256467 | A1 | * | 11/2005 | Conley ........................ 604/349 |
| 2007/0265586 | A1 |   | 11/2007 | Joshi          |

* cited by examiner

*Primary Examiner* — Melanie Hand
(74) *Attorney, Agent, or Firm* — Kelley Drye & Warren LLP

(57) ABSTRACT

The present invention relates to an apparatus for the removal and containment of human waste products from the effected area of incontinent patients. The apparatus and process encapsulates the areas of the body where urine and fecal matter are excreted. In particular, the present invention is directed to an apparatus for the containment and removal of human waste products, comprising: a receptacle; a vacuum connection to apply force for attaching the receptacle to the patient; and a vacuum dispersion membrane to provide mechanical support to the skin so as to minimize tensile force applied to the skin.

21 Claims, 4 Drawing Sheets

APPARATUS AND METHOD FOR THE REMOVAL AND CONTAINMENT OF HUMAN WASTE EXCRETION

CROSS-REFERENCE TO RELATED APPLICATIONS

The present invention relates to, and is entitled to the benefit of the earlier filing date and priority of U.S. Application No. 61,181,590 filed May 27, 2009, which is herein incorporated by reference as if fully set forth.

FIELD OF THE INVENTION

The present invention relates to a noninvasive apparatus and process for the removal and containment of human waste excretion by collecting and flushing bodily excretions away from the patient while maintaining a high degree of cleanliness within the effected area. This process is made possible through the use of a receptacle that is effectively attached to the patient using vacuum. The vacuum also serves as a seal for isolating the treated region from the outside environment. A flushing process is then contained within the treatment region so as to keep the effected area clean and moisturized. An embodiment of this invention may be applied to individuals who have undergone ostomy surgeries, whereby a vacuum seal can be used to enhance the attachment of an excrement collection device (such as, but not limited to, an ostomy bag) and provide sealing capability of the collection device so as to help prevent leakage. One novel aspect of an embodiment of this invention is the application of vacuum beneath a porous membrane that makes contact with the skin. The presence of vacuum and the porous membrane allows for attachment of the apparatus to the patient with minimal stress applied to the skin that could otherwise be injurious.

BACKGROUND OF THE INVENTION

Incontinence patients, due to the condition of not being able to control the bodily excretion of urine and fecal matter, are often faced with treatment options that have major adverse side effects. For bed-ridden patients, treatment options often include the utilization of diapers, diaper-like garments or other methods that result in skin exposure to urine and fecal matter. Considering the unpleasant presence of odor and soiled linens, along with prevalent breakdown of the skin, which often causes open wounds and infection, there is a need to provide a more effective and economical treatment for incontinent patients. There is also a need to provide a treatment option for those under "end of life" care where comfort and dignity is paramount. The later scenario often involves in-home treatment by family members whose physical and emotional strains are further impacted by the physical demands of frequent diaper replacement and associated cleaning routines of these body areas. These cleansed skin areas typically degrade due to exposure to urine and fecal matter, often resulting in contaminated open wounds. The implementation of the fully automated apparatus and processes embodied herein offers a dignified, highly efficient, labor free and cost effective means of treating this condition with dignity, while alleviating the physical demands and sleep interruption associated with the changing of diapers.

The use of catheters for treating urinary incontinence often results in pain and high exposure to infection. The implementation of the fully automated apparatus and processes embodied herein offers a comfortable alternative to catheters while minimizing exposure to infection.

There is a large population of spinal and brain injury patients that require complete immobility over a long term. Once some degree of mobility is restored, these patients typically endure many months of wound care treatment to repair skin breakdown attributed to exposure to bodily excretions. The apparatus and processes embodied herein would eliminate the need for follow-on wound care once mobility is restored.

The physical lift demands and spillage associated with obese patients utilizing bed pans could be simply eliminated through the use of the apparatus and processes embodied herein.

There is a large population of ostomy patients who are plagued with prevalent odor and bag leakage problems as well as skin irritations. These issues could be easily and cost effectively resolved through the use of the apparatus embodied herein.

It is therefore an advantage of some, but not necessarily all, embodiments of the present invention to provide an apparatus and process for the flushing of human waste products within the effected area that provides patient comfort, preserves skin integrity, reduces wound care and alleviates physical exertion of care givers associated with changing diapers and cleaning affected areas.

Additional advantages of various embodiments of the invention are set forth, in part, in the description that follows and, in part, will be apparent to one of ordinary skill in the art from the description and/or from the practice of the invention.

SUMMARY OF THE INVENTION

Responsive to the foregoing challenges, Applicant has developed an innovative apparatus for the removal and containment of human waste products from a patient comprising a receptacle having an interior and an exterior surface, a vacuum connection extending from the exterior surface to the interior surface of the receptacle to apply vacuum for attaching the receptacle to the patient, and a vacuum dispersion membrane disposed at the intersection of the vacuum connection and the patient to provide mechanical support to the skin and to minimize tensile force applied to the skin at the point of attachment of the receptacle. The apparatus may also comprise one or more of an inlet extending from the exterior surface to the interior surface of the receptacle for introducing a flushing fluid to an interior of the receptacle, a nozzle disposed on the interior surface of the receptacle and in fluid communication with the inlet for dispersing the flushing fluid within the receptacle, and/or an outlet extending from the interior surface to the exterior surface of the receptacle allowing fluids, gasses and contaminants to exit the receptacle.

The apparatus or receptacle may attached to a collection device, wherein the collection device is an ostomy bag, and further comprise a port disposed on the exterior surface of the receptacle. The vacuum dispersion membrane may be a textile, natural, synthetic, a polymer, or any other suitable material. The apparatus may further comprise a fecal detector for sensing the presence of fecal matter in the receptacle.

An embodiment of the present invention is an apparatus for the removal and containment of human waste products from a patient comprising a receptacle having an interior and an exterior surface, an inlet extending from the exterior surface to the interior surface of the receptacle for introducing a flushing fluid to an interior of the receptacle, an outlet extending from the exterior surface to the interior surface of the receptacle allowing fluids, gasses and contaminants to exit the receptacle, a vacuum connection extending from the exterior surface to the interior surface of the receptacle to apply vacuum for attaching the receptacle to the patient, and a vacuum dispersion membrane disposed at the intersection of the vacuum connection and the patient's skin to provide mechanical support to the skin so as to minimize tensile force applied to the skin. The apparatus my further comprise a nozzle disposed on the interior surface of the receptacle and in fluid communication with the inlet for dispersing the flushing fluid within the receptacle and/or a fecal detector for sensing the presence of fecal matter in the receptacle. The receptacle may be attached to a collection device, and the collection device may be an ostomy bag.

An embodiment of the present invention is an apparatus for the removal and containment of human waste products from a patient comprising a receptacle having an interior and an exterior surface, an inlet extending from the exterior surface to the interior surface of the receptacle for introducing a flushing fluid to an interior of the receptacle, a nozzle disposed on the interior surface of the receptacle and in fluid communication with the inlet for dispersing the flushing fluid within the receptacle, an outlet extending from the exterior surface to the interior surface of the receptacle allowing fluids, gasses and contaminants to exit the receptacle, a vacuum connection extending from the exterior surface to the interior surface of the receptacle to apply vacuum for attaching the receptacle to the patient, and a vacuum dispersion membrane disposed at the intersection of the vacuum connection and the patient's skin to provide mechanical support to the skin so as to minimize tensile force applied to the skin.

An embodiment of the present invention is an innovative apparatus for the removal and containment of human waste products from the effected area, comprising a receptacle that attaches to the body; an inlet for introducing flushing fluids and air flow; an outlet for the drainage of flushing fluid, bodily excretions and gases; and a vacuum seal for attaching and holding the receptacle in place, while isolating the internal receptacle region from the outside environment. It is worth noting that an antimicrobial cleaning agent could be used as a flushing fluid. It is also important to note that the vacuum seal and membrane according to an embodiment of the invention are well suited for improving the attachment and sealing aspects of ostomy interfaces between the skin and excrement collection devices such as ostomy bags.

Applicant has also developed an innovative method for mixing the flushing fluid with air so as to enhance solubility of excretions while minimizing the consumption of flushing fluids. The flushing fluid is a mixture of components that may supply nutrients, moisturizers and antimicrobial solutions to the skin and is designed to provide a protective layer over the skin to serve as a barrier against contaminants and irritants.

The present invention relates to an apparatus for the removal and containment of human waste products from the effected area of incontinent patients. The apparatus and process encapsulates the areas of the body where urine and fecal matter are excreted, flushes contaminants from the area and cleanses these areas. The flushing media may be an antimicrobial cleanser and/or contain nutrients that clean, moisturize and protect the skin from contamination. The process is controlled using an automated system controller. In particular, the present invention is directed to an apparatus for the containment and removal of human waste products, comprising: a receptacle; an inlet for introducing a flushing fluid to the interior of the receptacle; a nozzle arrangement for dispersing the flushing fluid within the receptacle; an outlet for fluids, gasses and contaminants to exit the receptacle; a vacuum connection to apply force for attaching the receptacle to the patient; a vacuum dispersion membrane to provide mechanical support to the skin so as to minimize tensile force applied to the skin; and a fecal detector for sensing the presence of fecal matter internal to the receptacle Embodiments of the present invention also relate to an apparatus for attaching and sealing an excrement collection device (ostomy bag) to the exterior skin of the human body. This allows for reliable sealing and containment of liquids, solids and gases coupled with easy removal and reattachment of the collection device. The apparatus may comprise a receptacle comprising an interface flange for attachment of an ostomy bag or may be a single unit having an interface flange integral to the ostomy bag. A vacuum dispersion membrane may be employed to minimize tensile stress of the skin. A means of easily dispersing antimicrobial, moisturizing and nutrients to the stoma may be employed so as to maintain hygiene and physical integrity of the stoma and surrounding skin if exposed. An adsorption provision for containing vapor leakage (odors) may be employed. The apparatus may have an integral vacuum control unit so as to eliminate the need for a tethered vacuum source.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention and, together with the detailed description, serve to explain the principles of the present invention.

BRIEF DESCRIPTION OF THE DRAWINGS

In order to assist the understanding of this invention, reference will now be made to the appended drawings, in which like reference characters refer to like elements. The drawings are exemplary only, and should not be construed as limiting the invention.

DETAILED DESCRIPTION OF EMBODIMENTS OF THE INVENTION

Figure 1:
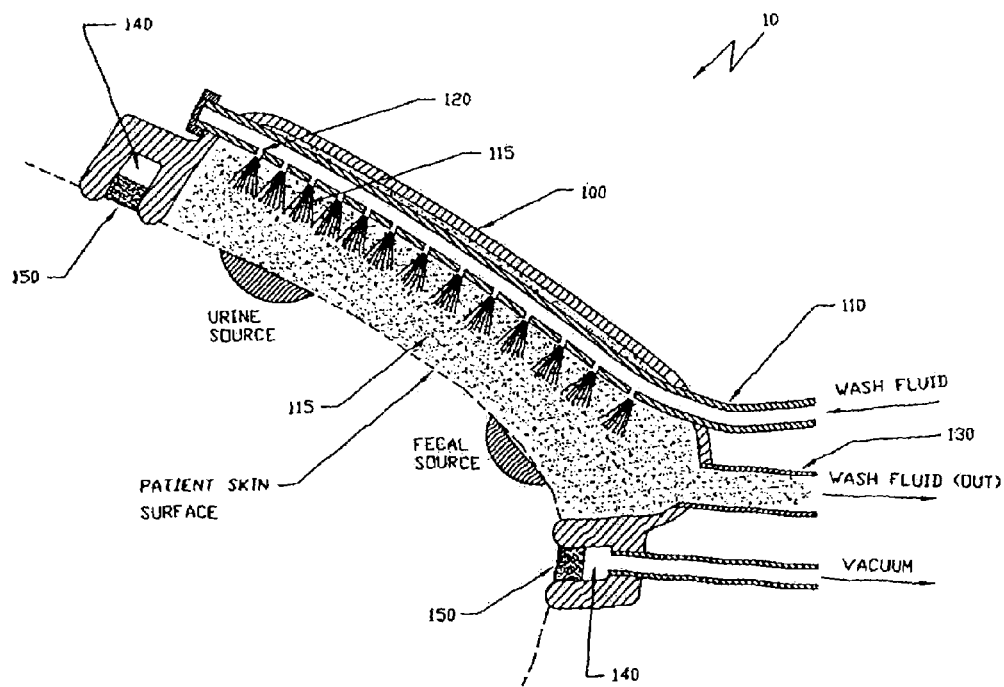
FIG. 1 is a cross-sectional view of an apparatus for the removal and containment of human waste products from the effected area in accordance with an embodiment of the present invention, depicting the female receptacle and its associated components.

Reference will now be made in detail to an embodiment of the present invention, an example of which is illustrated in the accompanying drawings. With reference to FIG. 1, apparatus 10 for the removal and containment of human waste products from the effected area may comprise receptacle 100 having an interior surface facing the patient's skin and an exterior surface facing away from the patient's skin, with inlet 110 extending from the exterior surface to the interior surface of receptacle 100 for introducing flushing fluids 115 (which may or may not be mixed with air) into the interior of receptacle 100, nozzle 120 disposed on the interior surface of receptacle 100 and in fluid communication with inlet 110 for introducing and dispersing flushing fluid 115 into the interior of receptacle 100, and outlet 130 extending from the exterior surface to the interior surface of receptacle 100 for allowing fluids, gasses and/or contaminants to exit from the interior of receptacle 100. Apparatus 10 also comprises vacuum connection 140 extending from the exterior surface to the interior surface of receptacle 100 so that vacuum may be applied between a portion of the interior surface of receptacle 100 and the patient's skin for sealing and holding receptacle 100 in place, and vacuum dispersion membrane 150 disposed at the interface of vacuum connection 140 to the patient's skin, to support the skin so as to minimize tensile force applied to the skin. Vacuum dispersion membrane 150 may be any suitable porous or permeable membrane allowing air, gas, fluid, etc. to pass through, while maintaining a structure that reduces the effect of a direct vacuum applied to the patient's skin. A lack of skin support will cause injury to the skin due to stretching. Applicant's invention helps preserve the condition of the skin by imposing minimal tensile force through the use of a porous membrane, beneath which, vacuum is applied. Vacuum dispersion membrane 150 may be a porous medium or a porous material comprising a solid, which may be referred to as a frame or matrix, permeated by an interconnected network of pores or voids which may be filled with a fluid (liquid or gas). Usually both the solid matrix and the pore network (also known as the pore space) are assumed to be continuous, so as to form two interpenetrating continua such as in a sponge. The membrane may be a natural material, synthetic, or of any other suitable composition. The membrane may be composed of a fabric, or cloth, or any other suitable textile, ceramic, polymer, and/or permeable and/or porous material. This feature is one aspect to avoiding injury to the skin.

Figure 2:
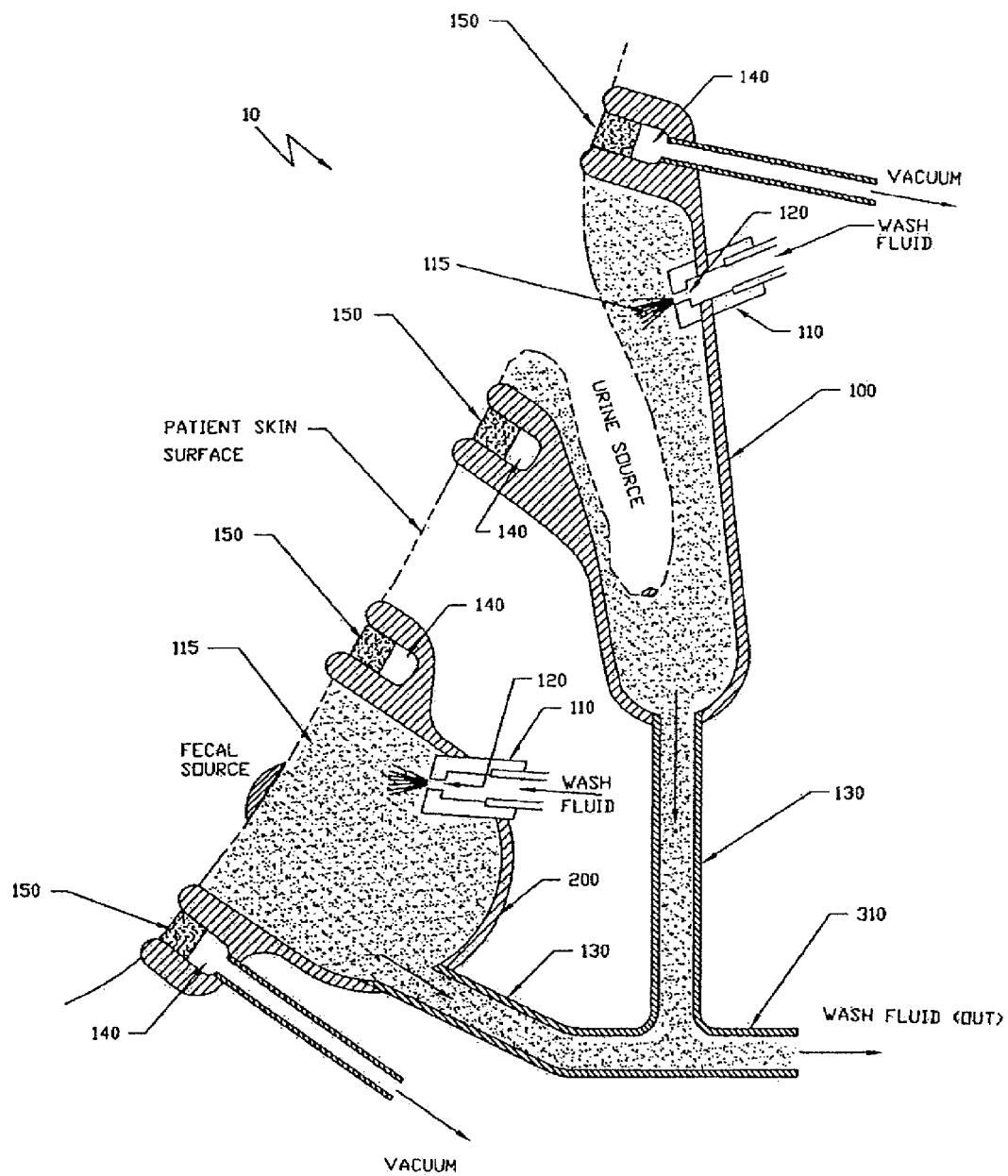
FIG. 2 is a cross-sectional view of an apparatus for the removal and containment of human waste products from the effected area in accordance with an embodiment of the present invention, depicting the male receptacle and its associated components.

With reference to FIG. 2, the apparatus 10 for the removal and containment of human waste products from the effected area, when configured for a male, may comprise two separate receptacles; receptacle 100 for the removal of male urine comprising inlet 110 for flushing fluids (which may or may not be mixed with air) to enter receptacle 100, nozzle 120 for dispersing flushing fluid 115 within receptacle 100, outlet 130 allowing fluids, gasses and/or contaminants to exit receptacle 100, vacuum connection 140 so that vacuum can be applied for holding receptacle 100 in place, and vacuum dispersion membrane 150 to support the skin so as to minimize tensile force applied to the skin, as described in detail above. A second receptacle 200 for receiving fecal excretion from a male patient may comprise inlet 110 for flushing fluids 115 (which may or may not be mixed with air) to enter receptacle 200, nozzle 120 for dispersing flushing fluid 115 within the receptacle, outlet 130 allowing fluids, air and/or contaminants to exit receptacle 200, vacuum connection 140 so that vacuum can be applied for sealing and holding receptacle 200 in place, and vacuum dispersion membrane 150 to distribute vacuum force to the skin so as to minimize tensile force applied to the skin, as described above. The outlets 130 of both receptacle 100 for male urine and second receptacle 200 for male feces may be operably connected so that single outlet tube can serve both receptacles.

Figure 3:
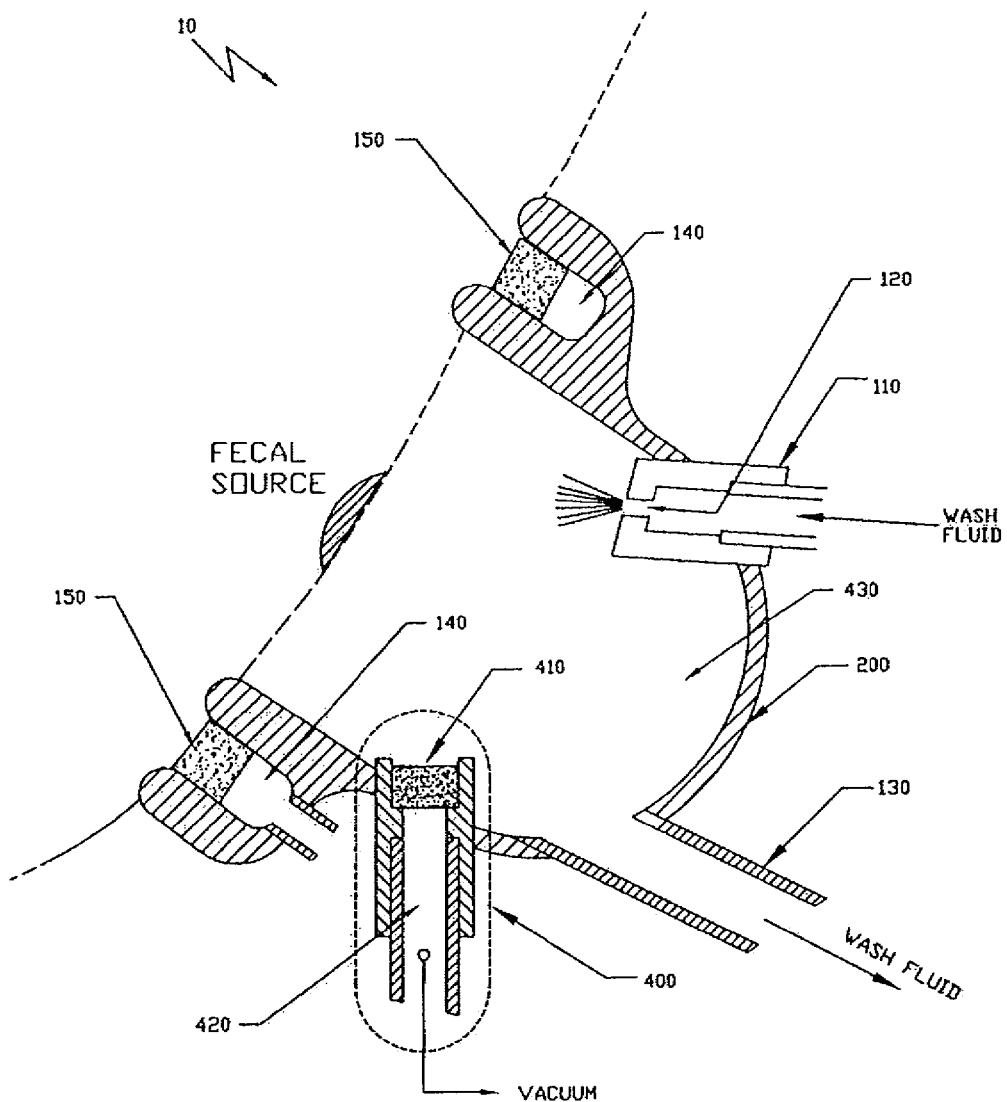
FIG. 3 is a cross-sectional view of an apparatus for the removal and containment of human waste products from the effected area in accordance with an embodiment of the present invention, depicting a fecal detector and its associated components.

With reference to FIG. 3, apparatus 400 for detecting fecal matter is an optional device which may be incorporated into receptacle 100 or 200 for patient applications involving significant fecal excretion rates. Apparatus 400 extends from the exterior surface to the interior surface of receptacle 100 and comprises detector chamber 420 and detector porous end 410.

A first end of detector chamber 420 is fluidly connected with a vacuum source at the exterior surface of receptacle 100. A second end of detector chamber 420 is in fluid communication with porous end 410. Porous end 410 fluidly connects detector chamber 420 to the interior of receptacle 100. Vacuum is applied to an internal region of detector 420 creating a flow of air from the interior of receptacle 100 through porous end 410. Pore size of porous end 410 is selected so that any concentration of air, water, urine or mist flowing through porous end 410 will result in an internal vacuum level below a set point. In the event that fecal matter accumulates on the outer surface of porous end 410, the pressure difference across porous end 410 increases. This increased pressure drop is attributed to the fecal matter having a greater viscosity than the air and/or water and/or urine and/or mist that is drawn through the porous end during a normal detection interval. This increase in pressure drop across porous end 410 results in an internal vacuum level above the set point thus initiating a flush cycle of interior region 430 of receptacle 100. During the flush cycle, wash fluid 115 is introduced through nozzle 120.

Figure 4:
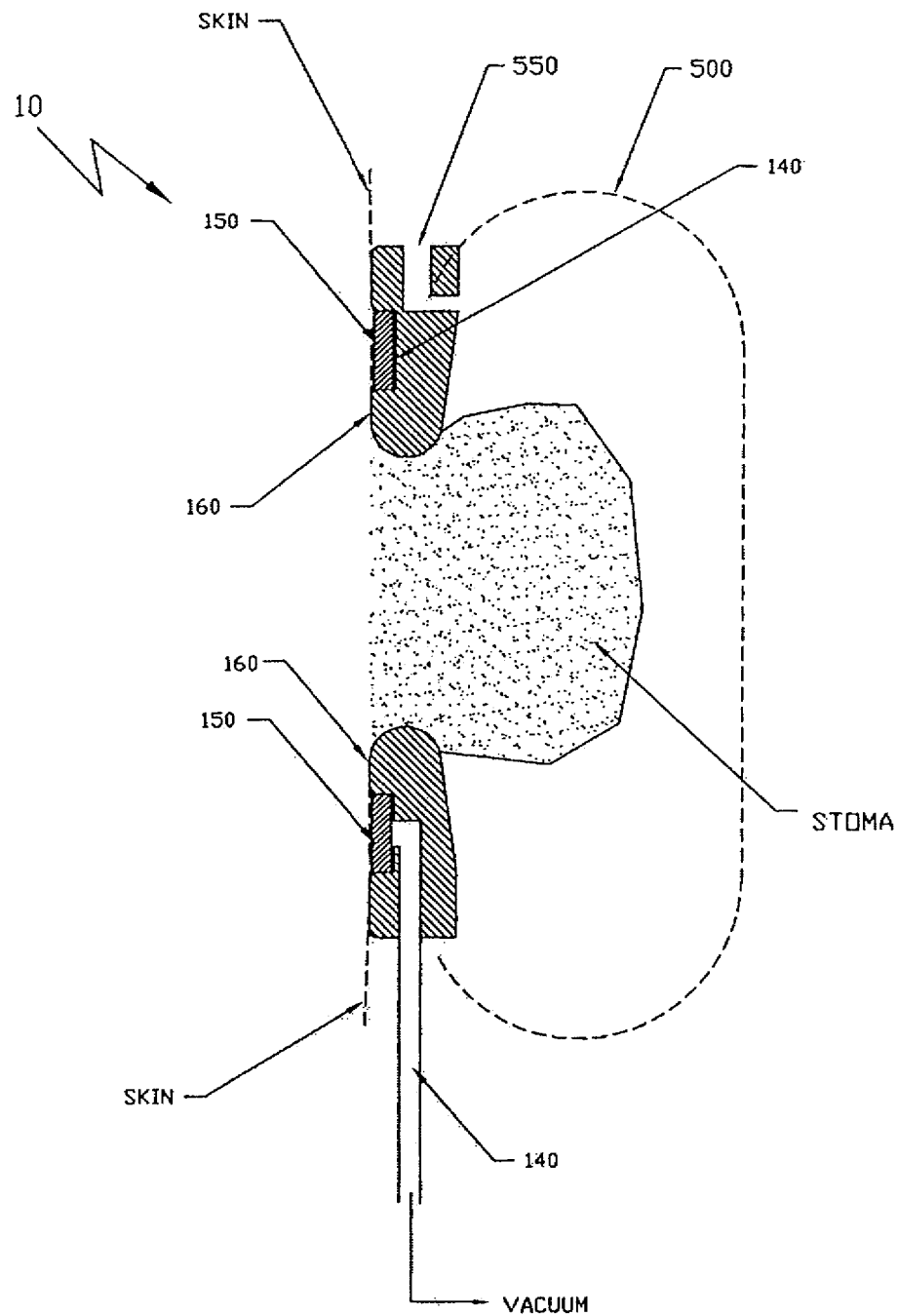
FIG. 4 is a cross-sectional view of an apparatus for attaching and sealing an excrement collection device (ostomy bag) in accordance with an embodiment of the present invention, depicting a sealing interface between the skin tissue and collection device (ostomy bag).

With reference to FIG. 4, apparatus 10 for the removal and containment of human waste products attaches and seals excrement collection device 500, such as, but not limited to, an ostomy bag, to the human body (exterior skin) and may comprise first surface of interface flange 160 permanently or removably attached to an opening in excrement collection device 500. Interface flange 160 and excrement collection device 500 form a unit wherein a second or interior surface of interface flange 160 attaches to the patient's skin around the circumference of an opening in the patient's body, such as, but not limited to, a stoma. Device 500 is attached to flange 160 to enable collection of fluids, gasses, and/or contaminants emanating from the patient's body. Another embodiment of apparatus 10 may comprise a single unit where interface flange 160 is an integral part of excrement collection device 500. The second or interior surface of interface flange 160 is attached to the patient's skin using vacuum connection 140 that extends from the interior surface to an exterior surface of flange 160, the exterior surface disposed between the patient's skin and device 500 and could be supplemented by adhesive and/or a belt to enhance support. The vacuum-to-skin interface comprises vacuum dispersion membrane 150 to support the skin so as to minimize tensile force applied to the skin while allowing the vacuum to attach the interior surface of flange 160 to the patient's skin. This feature is one aspect to avoiding injury to the skin.

Access port 550 may be disposed on an exterior surface of flange 160 in order to introduce antimicrobial, moisturizing and/or liquid barrier solutions and/or a connection point for adsorbent to contain odors. In one embodiment, vacuum connection 140 may comprise an integral vacuum control unit, comprised of a micro vacuum pump, switch, check valve and vacuum control switch/sensor (not shown) may be integrated as part of interface flange 160 so that vacuum can be supplied without tether of a separate vacuum source.

It will be apparent to those skilled in the art that variations and modifications of the present invention can be made without departing from the scope or spirit of the invention. Thus, it is intended that the present invention cover all such modifications and variations of the invention, provided they come within the scope of the appended claims and their equivalents.

What is claimed is:
1. An apparatus for the removal and containment of human waste products from a patient comprising:
    a receptacle having an interior and an exterior surface;

a vacuum connection extending from the exterior surface to the interior surface of the receptacle to apply vacuum for attaching the receptacle to the patient; and a vacuum dispersion membrane disposed at the intersection of the vacuum connection and the patient to provide mechanical support to the skin and to minimize tensile force applied to the skin at the point of attachment of the receptacle.

2. The apparatus of claim 1 comprising an inlet extending from the exterior surface to the interior surface of the receptacle for introducing a flushing fluid to an interior of the receptacle.

3. The apparatus of claim 2 comprising a nozzle disposed on the interior surface of the receptacle and in fluid communication with the inlet for dispersing the flushing fluid within the receptacle.

4. The apparatus of claim 1 comprising an outlet extending from the interior surface to the exterior surface of the receptacle allowing fluids, gasses and contaminants to exit the receptacle.

5. The apparatus of claim 1 wherein the receptacle is attached to a collection device.

6. The apparatus of claim 5 wherein the collection device is an ostomy bag.

7. The apparatus of claim 5 comprising a port disposed on the exterior surface of the receptacle.

8. The apparatus of claim 1 wherein the vacuum dispersion membrane is a polymer.

9. The apparatus of claim 1 comprising a fecal detector for sensing the presence of fecal matter in the receptacle.

10. An apparatus for the removal and containment of human waste products from a patient comprising:
   a receptacle having an interior and an exterior surface;
   an inlet extending from the exterior surface to the interior surface of the receptacle for introducing a flushing fluid to an interior of the receptacle;
   an outlet extending from the exterior surface to the interior surface of the receptacle allowing fluids, gasses and contaminants to exit the receptacle;
   a vacuum connection extending from the exterior surface to the interior surface of the receptacle to apply vacuum for attaching the receptacle to the patient; and
   a vacuum dispersion membrane disposed at the intersection of the vacuum connection and the patient's skin to provide mechanical support to the skin so as to minimize tensile force applied to the skin.

11. The apparatus of claim 10 comprising a nozzle disposed on the interior surface of the receptacle and in fluid communication with the inlet for dispersing the flushing fluid within the receptacle.

12. The apparatus of claim 10 comprising a fecal detector for sensing the presence of fecal matter in the receptacle.

13. The apparatus of claim 10 wherein the receptacle is attached to a collection device.

14. The apparatus of claim 13 wherein the collection device is an ostomy bag.

15. An apparatus for the removal and containment of human waste products from a patient comprising:
   a receptacle having an interior and an exterior surface;
   an inlet extending from the exterior surface to the interior surface of the receptacle for introducing a flushing fluid to an interior of the receptacle;
   a nozzle disposed on the interior surface of the receptacle and in fluid communication with the inlet for dispersing the flushing fluid within the receptacle;
   an outlet extending from the exterior surface to the interior surface of the receptacle allowing fluids, gasses and contaminants to exit the receptacle;
   a vacuum connection extending from the exterior surface to the interior surface of the receptacle to apply vacuum for attaching the receptacle to the patient; and
   a vacuum dispersion membrane disposed at the intersection of the vacuum connection and the patient's skin to provide mechanical support to the skin so as to minimize tensile force applied to the skin.

16. The apparatus of claim 15 wherein the vacuum dispersion membrane is a textile.

17. The apparatus of claim 15 wherein the vacuum dispersion membrane is synthetic.

18. The apparatus of claim 15 wherein the vacuum dispersion membrane is a polymer.

19. The apparatus of claim 15 comprising a fecal detector for sensing the presence of fecal matter in the receptacle.

20. The apparatus of claim 1 wherein the vacuum dispersion membrane is a textile.

21. The apparatus of claim 1 wherein the vacuum dispersion membrane is synthetic.

\* \* \* \* \*